United States Patent
Dyrstad et al.

(10) Patent No.: US 11,077,216 B2
(45) Date of Patent: *Aug. 3, 2021

(54) FORMULATION AND METHOD OF SYNTHESIS

(71) Applicant: GE Healthcare Limited, Buckinghamshire (GB)

(72) Inventors: Knut Richard Dyrstad, Oslo (NO); Torild Wickstrom, Oslo (NO); Thanushan Rajanayagam, Oslo (NO)

(73) Assignee: GE HEALTHCARE LIMITED, Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/318,599

(22) PCT Filed: Jun. 30, 2015

(86) PCT No.: PCT/EP2015/064796
§ 371 (c)(1),
(2) Date: Dec. 13, 2016

(87) PCT Pub. No.: WO2016/001199
PCT Pub. Date: Jan. 7, 2016

(65) Prior Publication Data
US 2017/0128597 A1 May 11, 2017

(30) Foreign Application Priority Data
Jun. 30, 2014 (GB) .................................. 1411569

(51) Int. Cl.
| | | |
|---|---|---|
| A61K 51/00 | (2006.01) | |
| A61M 36/14 | (2006.01) | |
| A61K 51/04 | (2006.01) | |
| C07B 59/00 | (2006.01) | |
| C07C 227/20 | (2006.01) | |

(52) U.S. Cl.
CPC ........ *A61K 51/0402* (2013.01); *C07B 59/001* (2013.01); *C07C 227/20* (2013.01); *C07B 2200/05* (2013.01); *C07C 2601/04* (2017.05)

(58) Field of Classification Search
CPC .......... A61K 51/0402; C07C 227/20; C07B 59/001; C07B 2200/05
USPC ...................................................... 424/1.89
See application file for complete search history.

(56) References Cited

U.S. PATENT DOCUMENTS

| | | |
|---|---|---|
| 8,182,788 B2 | 5/2012 | Knight et al. |
| 8,343,459 B2 | 1/2013 | Nakamura et al. |
| 8,790,620 B2 | 7/2014 | Hayashi et al. |
| 10,010,632 B2 | 7/2018 | Ito et al. |
| 2008/0076914 A1 | 3/2008 | Grigg et al. |
| 2008/0281121 A1 | 11/2008 | Ito et al. |
| 2009/0155166 A1 | 6/2009 | McBride et al. |
| 2009/0198085 A1 | 8/2009 | Hayashi et al. |
| 2012/0065365 A1 | 3/2012 | Chen et al. |

FOREIGN PATENT DOCUMENTS

| | | |
|---|---|---|
| AU | 2006262425 B2 | 12/2011 |
| CA | 2651786 A1 | 11/2007 |
| CN | 1646175 A | 7/2005 |
| CN | 101636183 A | 1/2010 |
| EP | 2119458 A1 | 11/2009 |
| JP | 2006500319 A | 1/2006 |
| JP | 2008-546783 A | 12/2008 |
| JP | 5159636 B2 | 3/2013 |
| JP | 5258583 B2 | 8/2013 |
| KR | 20090111331 A | 10/2009 |
| RU | 2008148851 A | 6/2010 |
| RU | 2428415 C2 | 9/2011 |
| WO | 2003090789 A1 | 6/2003 |
| WO | 03090789 A1 | 11/2003 |
| WO | 2007001958 A2 | 1/2004 |
| WO | 2005009393 A2 | 2/2005 |
| WO | 2006037950 A1 | 4/2006 |
| WO | 2008075522 A1 | 6/2008 |
| WO | 2008099800 A1 | 8/2008 |
| WO | 2012089594 A1 | 7/2012 |
| WO | 2013/053941 A1 | 4/2013 |
| WO | 2013/093025 A1 | 6/2013 |
| WO | 2013093025 A1 | 6/2013 |
| WO | 2013/144301 A2 | 10/2013 |
| WO | 2014023775 A1 | 2/2014 |

OTHER PUBLICATIONS

Nakao et al. App. Rad. Isot. 62 (2005) 889-895.*
Oh et al. Nucl. Med. Biol. 31 (2004) 803-809.*
Channing et al. Nuc. Med. Biol. 2001,28, 469-471.*
Gomzina et al. Radiochem. 2002, 44, 403-409.*
Svadberg et al., "Degradation of acetonitrile in eluent solutions for [18F]fluoride PET chemistry: impact on radiosynthesis of [18]FACBC and [18F]FDG", Journal of Labelled Compounds and Radiopharmaceuticals, vol. 55, 2012, pp. 97-102.
International Search Report and Written Opinion regarding International Application No. PCT/EP2015/064796, dated Sep. 15, 2015, 8 pages.
GE Search Report regarding GB Application No. 1411569.5, dated Mar. 31, 2015, 5 pages.
European Search Report corresponding to European Application No. 18187551.9, dated Jan. 21, 2019.
Intention to Grant Corresponding EP Application No. 18 187 551.9-1109 dated Sep. 7, 2020.
Japan Decision of Rejection corresponding to Japanese Application No. 2016-573925, dated Apr. 24, 2020 (with English translation).
Russian Office Action received in Application No. 2020123031.4 dated Nov. 20, 2020, 12 pages.

(Continued)

*Primary Examiner* — Michael G. Hartley
*Assistant Examiner* — Sean R Donohue
(74) *Attorney, Agent, or Firm* — Jeff B. Vockrodt; Culhane Meadows PLLC

(57) ABSTRACT

The present invention provides a composition comprising anti-1-amino-3-$^{18}$F-fluorocyclobutyl-1-carboxylic acid ($^{18}$F-FACBC) having an improved impurity profile compared with previous such compositions. Also provided is a method to obtain said composition.

16 Claims, 1 Drawing Sheet

(56) References Cited

OTHER PUBLICATIONS

Russian Search Report received in Application No. 2020123031.4 dated Jun. 30, 2015, 4 pages.
Chinese Office Action (Second) corresponding to CN Application No. 201280063530.X (PCT/EP2012/076689), dated Dec. 21, 2012.
Chinese Search Report corresponding to CN Application No. 201280063530.X, dated Dec. 21, 2012.
Decision to Grant a Patent for an Invention from the Patent Office of the Russian Federation (ROSPATENT), along with the corresponding English translation for Russian Patent Application No. 2014118755/15(029583), filed Dec. 12, 2012.
European Office Action corresponding to EP Application No. 12806500.0, dated Jan. 29, 2018.
European Search Report received Application No. 20196030.9-1109 dated Aug. 12, 2020, 6 pages.
Great Britain combined Search and Examination Report corresponding to GB Application No. GB1810553.6, dated Jul. 26, 2018.
International Search Report and Written Opinion corresponding to PCT Application No. PCT/EP2012/076689, dated Mar. 8, 2013.
Klok et al., Appl. Rad. Isot. 66 (2008) 203-207.
Korea Notice of Preliminary Rejection corresponding to KR Application No. 10-2014-7016663, dated Dec. 5, 2018.
Lasa et al., Tetrahedron: Asymmetry.
Lemaire et al., J. Label. Compd Radiopharm. 2002, 45, 435-447.
Mcconathy et al. Appl. Rad. Isot. 58 (2003) 657-666.
Meyeretal. Appl. Rad. Isoli 999, 51, 37-41.
Nakao, et al., Appl. Rad. Isot. 62 (2005) 889-895.
Stocking et al. Tetrahedron 57 (2001) 5303-5320.
Svadbert, et al., "Degradation of acetonitrile in eluent solutions for [18F]fluoride PET chemistry: impact on radiosynthesis of [18F]FACBC and [18F]FDG," Research Article, Oct. 20, 2011, 6 pages.
Vallabhajosula et al., Mol. Imaging: Radiopharm. PET and SPECT.
Wickstrom, et al., "The development of an automated and optimized synthesis of [18F] Fluciclovine on a FASTlab synthesizer utilizing chemometric design," The Journal of Nuclear Medicine, vol. 40, No. 2, 331-333, 2011.

* cited by examiner

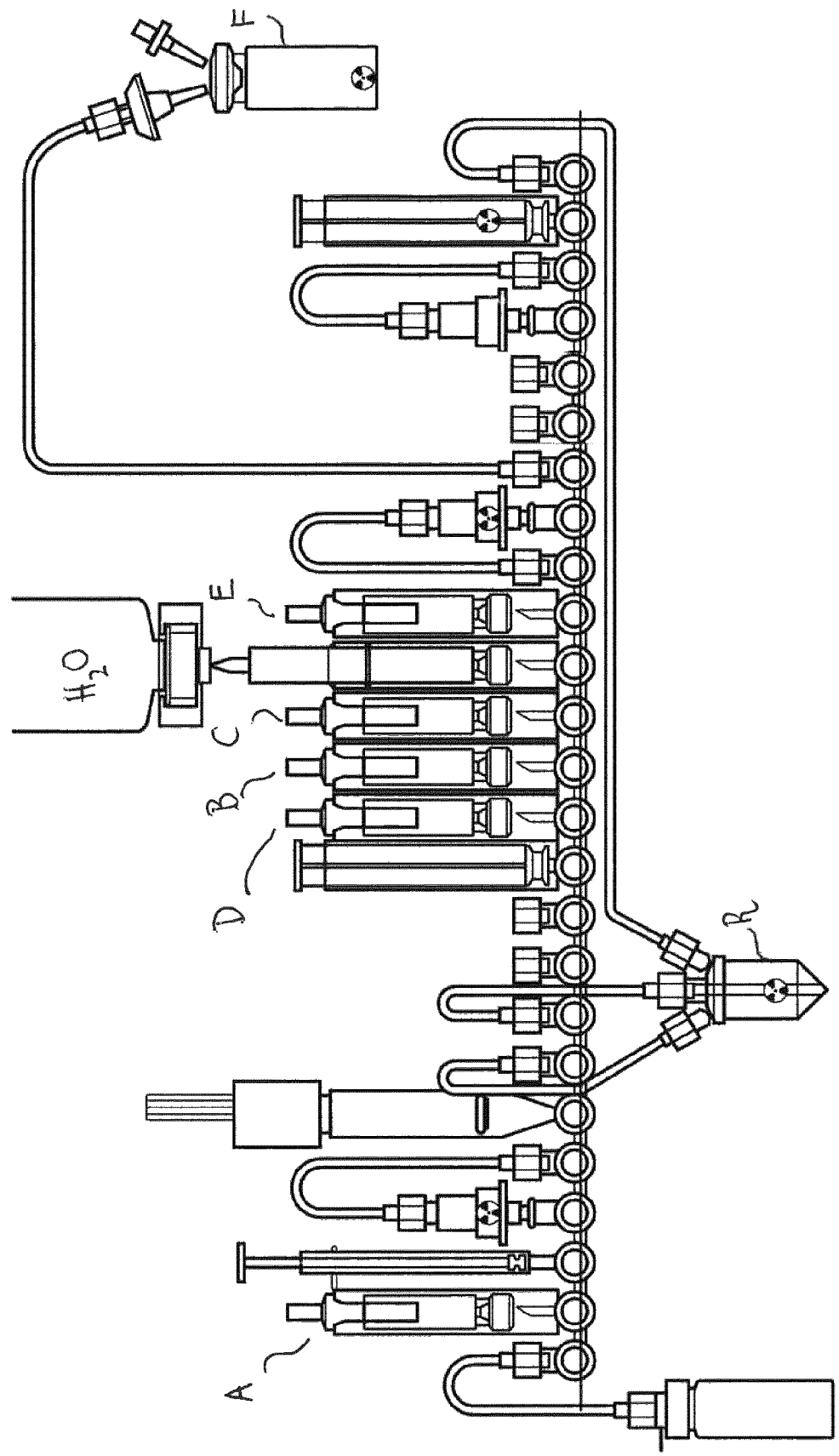

FORMULATION AND METHOD OF SYNTHESIS

CROSS-REFERENCE TO RELATED APPLICATIONS

This application is a filing under 35 U.S.C. 371 of international application number PCT/EP2015/064796, filed Jun. 30, 2015, which claims priority to GB application number 1411569.5, filed Jun. 30, 2014, the entire disclosures of each of which are hereby incorporated by reference.

TECHNICAL FIELD OF THE INVENTION

The present invention relates to a drug product composition and in particular to a composition comprising a positron emission tomography (PET) tracer. The composition of the present invention and its method of synthesis have certain advantages over the prior art.

DESCRIPTION OF RELATED ART

The non-natural amino acid $^{18}$F-1-amino-3-fluorocyclobutane-1-carboxylic acid ($^{18}$F-FACBC, also known as $^{18}$F-Fluciclovine) is taken up specifically by amino acid transporters and shows promise for positron emission tomography (PET) imaging of prostate cancer (Nanni et al 2014 Clinical Genitourinary Cancer; 12(2): 106-110). Production of $^{18}$F-FACBC comprises labelling of a triflate precursor compound with $^{18}$F-fluoride:

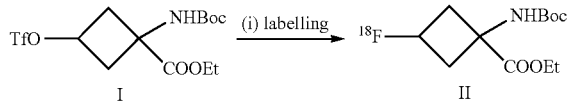

before removal of the two protecting groups:

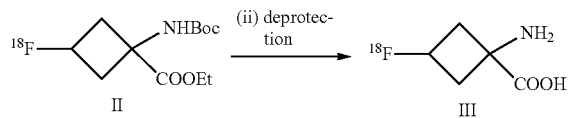

Following the deprotection steps purification is carried out to remove impurities. In the currently-practiced methods a combination of solid phases is used: ion retardation to remove excess Na$^+$ and excess left over from the deprotection steps, alumina to remove $^{18}$F-fluoride and a reversed phase to remove FACBC-related impurities such as 1-amino-3-hydroxyl-cyclobutane-1-carboxylic acid (hydroxyl-ACBC) and 1-amino-3-chloro-cyclobutane-1-carboxylic acid (chloro-ACBC).

The synthesis is currently typically carried out by means of an automated radiosynthesis procedure employing a so-called "cassette" or "cartridge" designed to fit removably and interchangeably onto an automated synthesis apparatus such as those that are commercially available from GE Healthcare, CTI Inc, Ion Beam Applications S.A. (Chemin du Cyclotron 3, B-1348 Louvain-La-Neuve, Belgium); Raytest (Germany) and Bioscan (USA). The cassette comprises all the reagents, reaction vessels and apparatus necessary to carry out the preparation of $^{18}$F-FACBC following introduction of suitably prepared $^{18}$F-fluoride by methods well-known in the field of PET tracer production.

A known cassette for the synthesis of $^{18}$F-FACBC is a FASTlab™ cassette from GE Healthcare. Each cassette is built around a one-piece-moulded manifold with 25 three-way stopcocks, all made of polypropylene. The cassette includes a quaternary methylammonium (QMA) solid phase extraction (SPE) cartridge, a 5 ml cyclic olefin copolymer reactor, one 1 ml syringe and two 5 ml syringes, spikes for connection with five prefilled reagent vials A-E, one water bag (100 ml), three SPE cartridges (tC18, HLB and alumina) and filters. The five FASTlab™ cassette reagent vials are filled as follows: vial A contains eluent solution comprising Kryptofix 2.2.2. and K$_2$CO$_3$ in acetonitrile (MeCN), vial B contains HCl, vial C contains MeCN, vial D contains dry precursor compound of Formula I from the above-illustrated reaction scheme and vial E contains NaOH. A known method for production of $^{18}$F-FACBC drug product using this FASTlab™ cassette is described in Example 1 of WO 2013/093025. The radiosynthesis is started by trapping aqueous $^{18}$F-fluoride onto the QMA followed by elution into the reactor using eluent from vial A, and then concentrated to dryness by azeotropic distillation with acetonitrile from vial C. Approximately MeCN is mixed with precursor compound from vial D and the dissolved precursor is added to the reactor and heated for 3 min at 85° C. The reaction mixture is then diluted with water and sent through the tC18 cartridge. The reactor is washed with water and sent through the tC18 cartridge. The labelled intermediate, fixed on the tC18 cartridge is washed with water, and then incubated with NaOH for 5 min to remove the ester group. The deesterified intermediate is eluted off the tC18 cartridge and back into the reactor using water. The BOC group is hydrolysed in the reactor by adding HCl and heating for 5 min at 60° C. The crude 18F-FACBC is then sent through the HLB (HLB=hydrophilic lipophilic balanced) cartridge for removal of FACBC-related impurities, the alumina cartridge for removal of $^{18}$F-fluoride, and thereafter into a 30 ml product vial containing citrate buffer. The HLB and alumina cartridges are then washed with water, which is sent to the product vial. Finally, NaOH and water are added to the product vial to provide the final purified formulation of $^{18}$F-FACBC. Prior to intravenous administration, this formulation is passed through a sterile filter.

The present inventors have found that the quality of the final $^{18}$F-FACBC drug product obtained using the above-described known FASTlab™ cassette and process can be somewhat variable. Residual acetonitrile levels have been found to range from about 100 μg/ml to about 600 μg/ml. While acceptable in terms of permitted daily exposure and in the context of the acceptance criteria for $^{18}$F-FACBC drug product, the amount and observed variability is less than ideal. Furthermore, residual aluminium have been found to range from about 7 μg/ml to nearly 20 μg/ml, which would mean a potential amount of 100 μg in a 5 ml $^{18}$F-FACBC injection. Where the $^{18}$F-FACBC drug product also comprises citrate buffer, complexes of aluminium and citrate are likely to be present, which is problematic as it is known that such complexes cross the blood-brain barrier (Rengel 2004 Biometals; 17: 669-689).

There is therefore scope to for an improved $^{18}$F-FACBC drug product formulation.

SUMMARY OF THE INVENTION

The present invention provides a drug product composition comprising $^{18}$F-FACBC that overcomes the problems seen with known such compositions. In particular, the composition of the present invention has an improved impurity profile, making it safer and more effective for imaging as compared with the prior art. Low and predictable levels of acetonitrile and/or aluminium in the final drug product mean that the composition of the invention more easily meets worldwide pharmacopeia requirements. In addition to a significant reduction in the concentration of aluminium in the final drug product, removal of the alumina cartridge has the allied advantages that a shorter and simplified process is permitted and that no particles arising from this cartridge are present, which the present inventors have noted can block the sterile filter used prior to injection of the drug product. Furthermore, the advantages of the present invention are achieved with only minor changes to the known process and without impairing the desirable qualities of known $^{18}$F-FACBC compositions.

DETAILED DESCRIPTION OF THE PREFERRED EMBODIMENTS

To more clearly and concisely describe and point out the subject matter of the claimed invention, definitions are provided in the detailed description hereinbelow for specific terms used throughout the present specification and claims. Any exemplification of specific terms herein should be considered as non-limiting examples.

In one aspect the present invention relates to a positron emission tomography (PET) tracer composition comprising anti-1-amino-3-$^{18}$F-fluorocyclobutyl-1-carboxylic acid ($^{18}$F-FACBC) characterised in that said composition comprises no more than 5.0 µg/mL dissolved aluminium (Al).

In one aspect the present invention relates to a positron emission tomography (PET) tracer composition comprising anti-1-amino-3-$^{18}$F-fluorocyclobutyl-1-carboxylic acid ($^{18}$F-FACBC) characterised in that said composition comprises no more than 5.0 µg/mL dissolved aluminium (Al) and no more than 50 µg/mL acetonitrile (MeCN).

In the context of the present invention a "PET tracer composition" refers to a composition comprising a PET tracer together with a biocompatible carrier in a form suitable for mammalian administration. The PET tracer composition of the invention is referred to hereunder also as the composition of the invention. A "PET tracer" is defined herein as a biologically active molecule comprising an atom which is a positron emitter suitable for intravenous administration to a mammalian subject followed by PET imaging to obtain one or more clinically-useful images of the location and/or distribution of the PET tracer. A "biocompatible carrier" as defined herein is a fluid, especially a liquid, in which a pharmaceutical is suspended or dissolved, such that the composition is physiologically tolerable, i.e. can be administered to the mammalian body without toxicity or undue discomfort. The biocompatible carrier is suitably an injectable carrier liquid such as sterile, pyrogen-free water for injection or an aqueous solution such as saline.

The compound "$^{18}$F-FACBC" is represented by the following chemical structure:

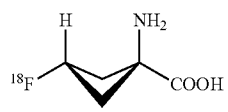

The term "not more than" as used herein should be understood to mean any amount less than and including the quoted quantity. In an idealized embodiment of the composition of the present invention there would be zero µg/mL of each impurity present. However, in reality, zero µg/mL of an impurity is unlikely and at least a trace amount of each impurity remains in the composition. The term "not more than" acknowledges that a trace amount of one or more impurities is present in a PET tracer composition, and defines a concentration limit above which the composition would not be deemed acceptable for use.

In one embodiment, the composition of the invention comprises not more than not more than 3.0 µg/mL dissolved Al, and in another embodiment not more than 1.5 µg/mL dissolved Al.

In one embodiment the composition of the present invention comprises MeCN at a concentration not more than 20 µg/mL.

The composition of the invention in one embodiment has an end of synthesis (EOS) radiochemical purity (RCP) of at least 95%, in another embodiment at least 98%, and in yet another embodiment at least 99%.

The term "end of synthesis" refers to the point in time when the labelled compound is collected in the product collection vial.

EP 2119458 (A1) teaches that a more stable formulation of $^{18}$F-FACBC is achieved when the pH is maintained within the range 2.0-5.9. As discussed in WO 2013/093025, use of citrate buffer allows the pH to be maintained within an even narrower range, provides resistance to degradation and enables the formulation to be autoclaved. In one embodiment, the composition of the present invention therefore comprises around 50-100 mM citrate buffer, in another embodiment around 60-90 mM citrate buffer and in yet another embodiment around 75-85 mM citrate buffer. The term "around" in this context incorporates the exact values of the ranges as well as a small variation around these values that would be expected by the skilled person to achieve the same stabilisation effect.

In another aspect, the present invention provides a method to prepare a PET tracer composition of the invention wherein said method comprises:

(a) reacting in a reaction vessel a source of $^{18}$F-fluoride with a precursor compound of Formula I:

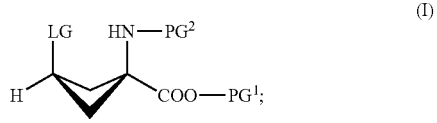

wherein:
LG is a leaving group;
PG$^1$ is a carboxy protecting group; and,
PG$^2$ is an amine protecting group;
to obtain a reaction mixture comprising a compound of Formula II:

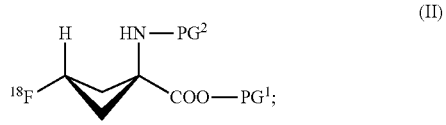

wherein PG$^1$ and PG$^2$ are as defined for Formula I;
(b) carrying out removal of PG$^1$ and PG$^2$ to obtain a reaction mixture comprising $^{18}$F-FACBC; and (c) purifying said reaction mixture comprising $^{18}$F-FACBC by passing it through a hydrophilic lipophilic balanced (HLB) solid phase, characterised in that said purifying does not comprise passing the reaction mixture comprising $^{18}$F-FACBC through an alumina solid phase.

In another aspect, the present invention provides a method to prepare a PET tracer composition of the invention wherein said method comprises:

(a) reacting in a reaction vessel a source of $^{18}$F-fluoride with a precursor compound of Formula I:

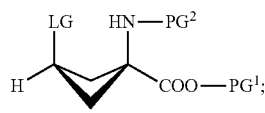

wherein:
LG is a leaving group;
PG$^1$ is a carboxy protecting group; and,
PG$^2$ is an amine protecting group;
wherein said reacting step is carried out in acetonitrile; to obtain a reaction mixture comprising a compound of Formula II:

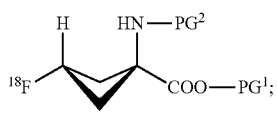

wherein PG$^1$ and PG$^2$ are as defined for Formula I;

(b) transferring said reaction mixture comprising said compound of Formula II out of said reaction vessel and carrying out removal of PG$^1$ to obtain a reaction mixture comprising a compound of Formula III:

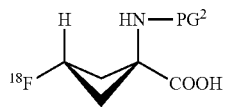

wherein PG$^2$ is as defined for Formula I;
(c) applying heat to said reaction vessel at the same time as carrying out removal of PG$^1$;
(d) transferring said reaction mixture comprising said compound of Formula III back into said reaction vessel and carrying out removal of PG$^2$ to obtain a reaction mixture comprising $^{18}$F-FACBC;
(e) purifying said reaction mixture comprising $^{18}$F-FACBC by passing it through a hydrophilic lipophilic balanced (HLB) solid phase, characterised in that said purifying does not comprise passing the reaction mixture comprising $^{18}$F-FACBC through an alumina solid phase.

The "source of $^{18}$F-fluoride" suitable for use in step (a) of the method of the invention is normally obtained as an aqueous solution from the nuclear reaction $^{18}$O(p,n)$^{18}$F. In order to increase the reactivity of fluoride and to reduce or minimise hydroxylated by-products resulting from the presence of water, water is typically removed from $^{18}$F-fluoride prior to the reaction, and fluorination reactions are carried out using anhydrous reaction solvents (Aigbirhio et al 1995 J Fluor Chem; 70: 279-87). A further step that is used to improve the reactivity of $^{18}$F-fluoride for radiofluorination reactions is to add a cationic counterion prior to the removal of water. Suitably, the counterion should possess sufficient solubility within the anhydrous reaction solvent to maintain the solubility of the $^{18}$F-fluoride. Therefore, counterions that are typically used include large but soft metal ions such as rubidium or caesium, potassium complexed with a cryptand such as Kryptofix™, or tetraalkylammonium salts, wherein potassium complexed with a cryptand such as Kryptofix™, or tetraalkylammonium salts are preferred.

The "precursor compound" for step (a) of the method of the invention comprises a non-radioactive derivative of a radiolabelled compound, designed so that chemical reaction with a convenient chemical form of the detectable label occurs site-specifically, can be conducted in the minimum number of steps (ideally a single step), and without the need for significant purification (ideally no further purification), to give the desired radiolabelled compound. Such precursor compounds are synthetic and can conveniently be obtained in good chemical purity.

A suitable "leaving group" in the context of the compound of Formula I in step (a) of the method of the present invention is a chemical group that can be displaced by nucleophilic displacement reaction with fluoride ion. These are well-known in the art of synthetic chemistry. In some embodiments the leaving group of the present invention is a linear or branched C$_{1-10}$ haloalkyl sulfonic acid substituent, a linear or branched C$_{1-10}$ alkyl sulfonic acid substituent, a fluorosulfonic acid substituent, or an aromatic sulfonic acid substituent. In other embodiments of the invention the leaving group is selected from methanesulfonic acid, toluenesulfonic acid, nitrobenzenesulfonic acid, benzenesulfonic acid, trifluoromethanesulfonic acid, fluorosulfonic acid, and perfluoroalkylsulfonic acid. In some embodiments the leaving group is either methanesulfonic acid, trifluoromethanesulfonic acid or toluenesulfonic acid and in another embodiment the leaving group is trifluoromethanesulfonic acid.

The term "protecting group" as used in connection with the substituents PG$^1$ and PG$^2$ refers to a group which inhibits or suppresses undesirable chemical reactions, but which is designed to be sufficiently reactive that it may be cleaved from the functional group in question to obtain the desired product under mild enough conditions that do not modify the rest of the molecule. Protecting groups are well known to those skilled in the art and are described in 'Protective Groups in Organic Synthesis', Theorodora W. Greene and Peter G. M. Wuts, (Fourth Edition, John Wiley & Sons, 2007).

The PG$^1$ "carboxy protecting group" herein is preferably linear or branched C$_{1-10}$ alkyl chain or an aryl substituent. The term "alkyl" used either alone or as part of another group is defined as any straight, branched or cyclic, saturated or unsaturated C$_n$H$_{2n+1}$ group. The term "aryl" refers to any C$_{6-14}$ molecular fragment or group which is derived from a monocyclic or polycyclic aromatic hydrocarbon, or a monocyclic or polycyclic heteroaromatic hydrocarbon. In one embodiment of the method of the invention PG$^1$ is selected from methyl, ethyl, t-butyl and phenyl. In another embodiment of the invention PG$^1$ is methyl or ethyl and in yet another embodiment PG$^1$ is ethyl.

The PG$^2$ "amine protecting group" herein refers to a chemical group that suitably prevents reaction between $^{18}$F and the amino group in the process of providing the compound of Formula II. Examples of suitable amine protecting groups include various carbamate substituents, various amide substituents, various imide substituents, and various amine substituents. Preferably, the amine protecting group is selected from the group consisting of linear or branched $C_{2-7}$ alkyloxycarbonyl substituents, linear or branched $C_{3-7}$ alkenyloxycarbonyl substituents, $C_{7-12}$ benzyloxycarbonyl substituents that may have a modifying group, $C_{2-7}$ alkyldithiooxycarbonyl substituents, linear or branched $C_{1-6}$ alkylamide substituents, linear or branched $C_{2-6}$ alkenylamide substituents, $C_{6-11}$ benzamide substituents that may have a modifying group, $C_{4-10}$ cyclic imide substituents, $C_{6-11}$ aromatic imine substituents that may have a substituent, linear or branched $C_{1-6}$ alkylamine substituents, linear or branched $C_{2-6}$ alkenylamine substituents, and $C_{6-11}$ benzylamine substituents that may have a modifying group. In some embodiments of the invention $PG^2$ is selected from t-butoxycarbonyl, allyloxycarbonyl, phthalimide, and N-benzylideneamine. In other embodiments $PG^2$ is selected from t-butoxycarbonyl or phthalimide. In one embodiment of the invention $PG^2$ is t-butoxycarbonyl.

The term "reacting" in step (a) of the method of the invention as is well known to those of skill in the art refers to bringing two or more chemical substances (typically referred to in the art as "reactants" or "reagents") together to result in a chemical change in one or both/all of the chemical substances.

The "removal of $PG^1$" in step (b) of the method of the invention is suitably carried out by contacting the compound of Formula II, comprised within the reaction mixture obtained in step (a), with a carboxy deprotecting agent. A suitable carboxy deprotecting agent may be either an acid or an alkaline solution, as is well-known to the skilled person (see Greene and Wuts, supra). The concentration of the carboxy deprotecting agent is suitably just sufficient to remove the carboxy protecting group. Preferably the carboxy deprotecting agent is an alkaline solution. In certain embodiments the carboxy deprotecting agent is a sodium hydroxide or a potassium hydroxide solution and in a preferred embodiment is a sodium hydroxide solution, for example of 0.5-2.0M. The temperature and the duration used for deprotection may in some embodiments be tailored to permit removal of $PG^1$. For example, in certain embodiments the reacting step is carried out at room temperature and for a duration of around 1-5 minutes. In one embodiment, removal of $PG^1$ is carried out by passing the reaction mixture comprising the compound of Formula II through a solid phase extraction (SPE) column where the compound of Formula II binds to the solid phase. Once the compound of Formula II is bound, the outlet of the SPE column is closed so that the carboxy deprotecting agent is retained therein for a defined amount of time. A suitable solid phase for use in this manner is a reversed phase solid phase, e.g. tC18.

Step (c) comprises applying heat to the reaction vessel using methods well-known to those of skill in the art, e.g. using a dedicated heater into which the reaction vessel is placed for the duration of the radiosynthesis. The application of heat must be so that the reaction vessel can be used for the subsequent step (d), i.e. so that the reaction vessel is intact and undamaged, and also so that residual solvent is effectively removed. This step (c) is carried out at the same time as removal of $PG^1$, i.e. after the reaction mixture comprising the compound of Formula II has been transferred out of said reaction vessel. A suitable temperature for this heating step should be no greater than the tolerance of the reaction vessel, e.g. for a reaction vessel made from cyclic olefin copolymer (COC) a temperature of no greater than about 130° C. and for a reaction vessel made from polyetheretherketone (PEEK) a temperature of no greater than about 200° C. For convenience, the temperature used to heat the reaction vessel in step (c) may be selected to be as close as possible to the temperature used during the labelling step (a). Suitable temperatures for radiolabelling step (a) are in the range of about 80-140° C., in other embodiments 85-130° C.

The "removal of $PG^2$" in step (d) of the method of the invention is carried out by contacting the compound of Formula III with an amine deprotecting agent. A suitable amine deprotecting agent may be either an acid or an alkaline solution, as is well-known to the skilled person (see Greene and Wuts, supra). The concentration of the amine deprotecting agent is suitably just sufficient to remove $PG^2$. Preferably the amine deprotecting agent is an acid solution. A suitable acid is an acid selected from inorganic acids such as hydrochloric acid (HCl), sulfuric acid ($H_2SO_4$) and nitric acid ($HNO_3$), and organic acids such as perfluoroalkyl carboxylic acids, e.g. trifluoroacetic acid ($CF_3CO_2H$). In certain embodiments, the amine deprotecting agent is HCl, e.g. at a concentration of 1.0-4.0M. Removal of $PG^2$ is in one embodiment carried out with heat to allow the deprotection to proceed more rapidly. The time depends on the reaction temperature or other conditions. For example, in one embodiment removal of $PG^2$ is carried out at 60° C., with a reaction time of 5 minutes.

The aim of the "purifying" step (e) is to obtain substantially pure $^{18}F$-FACBC. The term "substantially" refers to the complete or nearly complete extent or degree of an action, characteristic, property, state, structure, item, or result. The term "substantially pure" as used herein in the context of $^{18}F$-FACBC encompasses completely pure $^{18}F$-FACBC or $^{18}F$-FACBC that is sufficiently pure to be suitable for use as a PET tracer. The term "suitable for use as a PET tracer" means that the purified $^{18}F$-FACBC product is suitable for intravenous administration to a mammalian subject followed by PET imaging to obtain one or more clinically-useful images of the location and/or distribution of $^{18}F$-FACBC.

A "HLB solid phase" is a reversed phase solid phase having hydrophilic and lipophilic components suitable for a range of purposes. HLB solid phase is commercially-available as SPE cartridges suitable for use in the method of the present invention, e.g. the Oasis HLB SPE cartridge.

An "alumina solid phase" is an aluminium oxide normal phase solid phase routinely used in $^{18}F$ labelling methods as a means to remove free $^{18}F$-fluoride and optimise the radiochemical purity of the final product. Alumina solid phase is commercially-available as SPE cartridges suitable for use in the method of the present invention, e.g. the Waters Alumina N Light.

In the method of the invention, steps (a)-(c) or (a)-(e) are carried out in sequence.

In one embodiment of the method of the present invention, the substituent LG in the compound of Formula I is a linear or branched $C_{1-10}$ haloalkyl sulfonic acid substituent, a linear or branched $C_{1-10}$ alkyl sulfonic acid substituent, a fluorosulfonic acid substituent, or an aromatic sulfonic acid substituent. Examples of LG include methanesulfonic acid, toluenesulfonic acid, nitrobenzenesulfonic acid, benzenesulfonic acid, trifluoromethanesulfonic acid, fluorosulfonic acid, and perfluoroalkylsulfonic acid. In one embodiment LG is trifluoromethanesulfonic acid.

In one embodiment of the method of the present invention the substituent $PG^1$ in the compounds of Formula I and II is a linear or branched $C_{1-10}$ alkyl chain or an aryl substituent.

For example, $PG^1$ can be methyl, ethyl, t-butyl or phenyl. In one embodiment $PG^1$ is methyl or ethyl. In another embodiment, $PG^1$ is ethyl.

In one embodiment of the method of the present invention the substituent $PG^2$ in the compounds of Formulas I-III is a carbamate substituent, an amide substituent, an imide substituent or an amine substituent. Examples include t-butoxycarbonyl, allyloxycarbonyl, phthalimide, and N-benzylideneamine. In one embodiment, $PG^2$ is t-butoxycarbonyl.

The method of the present invention may further comprise the step of formulating the purified reaction mixture obtained in step (e) with citrate buffer. In one embodiment, this formulating step results in a concentration of 50-100 mM citrate buffer, in another embodiment 60-90 mM citrate buffer and in yet another embodiment 75-85 mM citrate buffer.

In one embodiment, the method of the invention is automated, e.g. carried out on an automated synthesis apparatus. $^{18}$F-labelled PET tracers are often conveniently prepared on automated radiosynthesis apparatus. By the term "automated radiosynthesis apparatus" is meant an automated module based on the principle of unit operations as described by Satyamurthy et al (1999 Clin Positr Imag; 2(5): 233-253). The term "unit operations" means that complex processes are reduced to a series of simple operations or reactions, which can be applied to a range of materials. Suitable automated synthesiser apparatus are commercially available from a range of suppliers including: GE Healthcare Ltd (Chalfont St Giles, UK); CTI Inc. (Knoxville, USA); Ion Beam Applications S.A. (Chemin du Cyclotron 3, B-1348 Louvain-La-Neuve, Belgium); Raytest (Straubenhardt, Germany) and Bioscan (Washington D.C., USA).

Commercial automated radiosynthesis apparatus also provide suitable containers for the liquid radioactive waste generated as a result of the radiopharmaceutical preparation. Automated radiosynthesis apparatus are not typically provided with radiation shielding, since they are designed to be employed in a suitably configured radioactive work cell. The radioactive work cell, also termed a hot cell, provides suitable radiation shielding to protect the operator from potential radiation dose, as well as ventilation to remove chemical and/or radioactive vapours.

Preferred automated radiosynthesis apparatus of the present invention are those which interact with a disposable or single use "cassette" (also commonly referred to as a "cartridge") which comprises all the reagents, reaction vessels and apparatus necessary to carry out the preparation of a given batch of radiopharmaceutical. By use of such cassettes the automated radiosynthesis apparatus has the flexibility to be capable of making a variety of different radiopharmaceuticals with minimal risk of cross-contamination, by simply changing the cassette. The cassette approach also has the advantages of: simplified set-up and hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

The cassette has been simplified by removal of the alumina cartridge. The alumina cartridge was present in prior cassette configurations to remove residues of free $^{18}$F-fluoride from insufficient purification and/or from radiolysis. However, the present inventors have found that the rest activity on the alumina cartridge is very low (0.1-0.3%) indicating both a robust purification process and a low degree of radiolysis. These data suggest that the alumina cartridge is superfluous and can be removed. This has the additional benefit of there being no risk of any particles from the alumina cartridge being present in drug product, which pose a risk of blocking the sterile filter.

The process has been improved by the addition of a concurrent step of removal of residual acetonitrile from the reactor while the deesterification step proceeds on the tC18 cartridge. This results in a final drug product having a lower and more predictable concentration of residual acetonitrile than that obtained using prior art methods.

BRIEF DESCRIPTION OF THE FIGURES

FIG. 1 illustrates an exemplary cassette to carry out the method of the invention.

BRIEF DESCRIPTION OF THE EXAMPLES

The following non-limiting examples serve to illustrate particular embodiments of the subject matter of the present invention.

LIST OF ABBREVIATIONS USED IN THE EXAMPLES

BOC tert-Butyloxycarbonyl
DP drug product
HLB hydrophobic-lipophilic balance
$K_{222}$ Kryptofix 222
MeCN acetonitrile
QMA quaternary methyl ammonium
RAC radioactive concentration
RCP: radiochemical purity

EXAMPLES

Comparative Example 1: Prior Art Synthesis of $^{18}$F-FACBC

1(i) FASTlab Cassette

All radiochemistry was performed on a commercially-available GE FASTlab™ with single-use cassettes. Each cassette is built around a one-piece-moulded manifold with 25 three-way stopcocks, all made of polypropylene. Briefly, the cassette includes a 5 ml reactor (cyclic olefin copolymer), one 1 ml syringe and two 5 ml syringes, spikes for connection with five prefilled vials, one water bag (100 ml) as well as various SPE cartridges and filters. Fluid paths are controlled with nitrogen purging, vacuum and the three syringes. The fully automated system is designed for single-step fluorinations with cyclotron-produced $^{18}$F-fluoride. The FASTlab was programmed by the software package in a step-by-step time-dependent sequence of events such as moving the syringes, nitrogen purging, vacuum, and temperature regulation. Vial A contained $K_{222}$ (58.8 mg, 156 μmol), $K_2CO_3$ (8.1 mg, 60.8 μmol) in 79.5% (v/v) $MeCN_{(aq)}$ (1105 μl). Vial B contained 4M HCl (2.0 ml). Vial C contained MeCN (4.1 ml). Vial D contained the precursor (48.4 mg, 123.5 μmol) in its dry form (stored at −20° C. until cassette assembly). Vial E contained 2 M NaOH (4.1 ml). The 30 ml product collection glass vial was filled with 200 mM trisodium citrate (10 ml).

1(ii) Production of $^{18}$F-Fluoride

No-carrier-added $^{18}$F-fluoride was produced via the $^{18}$O (p,n)$^{18}$F nuclear reaction on a GE PETtrace 6 cyclotron (Norwegian Cyclotron Centre, Oslo). Irradiations were performed using a dual-beam, 30 µA current on two equal Ag targets with HAVAR foils using 16.5 MeV protons. Each target contained 1.6 ml of >96% [$^{18}$O]water (Marshall Isotopes). Subsequent to irradiation and delivery to a hotcell, each target was washed with [$^{16}$O]water (Merck, water for GR analysis). Aqueous $^{18}$F-fluoride was passed through the QMA and into the $^{18}$O—H$_2$O recovery vial. The QMA was then flushed with MeCN and sent to waste.

1(iii) $^{18}$F-Fluoride Labelling

The trapped $^{18}$F-fluoride was eluted into the reactor using eluent from vial A and then concentrated to dryness by azeotropic distillation with acetonitrile (vial C). MeCN was mixed with precursor in vial D from which the dissolved precursor was added to the reactor and heated to 85° C.

1(iv) Removal of Ester Protecting Group

The reaction mixture was diluted with water and sent through the tC18 cartridge. Reactor was washed with water and sent through the tC18 cartridge. The labelled intermediate, fixed on the tC18 cartridge was washed with water, and then incubated with 2M NaOH after which the 2M NaOH was sent to waste.

1(v) Removal of BOG Protecting Group

The labelled intermediate (without the ester group) was then eluted off the tC18 cartridge into the reactor using water. The BOC group was hydrolysed by adding 4M HCl and heating the reactor.

1(vi) Purification

The reactor content with the crude $^{18}$F-FACBC was sent through the HLB and Alumina cartridges and into the 30 ml product vial. The HLB and Alumina cartridges were washed with water and collected in the product vial.

1(vii) Formulation

2M NaOH and water was added to the product vial, giving a purified drug product (DP) with a total volume of 26 ml.

1(viii) Acetonitrile Concentration

Acetonitrile (MeCN) concentration was determined using a gas chromatographic system with FID, an automated liquid injector, a fused silica capillary column with USP stationary phase G43 (6% cyanopropylphenyl-94% dimethyl polysiloxane) and a reporting integrator or data system with reintegration capacity. 1000 µg/ml of MeCN was used as a standard. Blank was prepared by transferring 1 ml of purified water to a 2 ml GC crimp cap vial, which was capped immediately. 1 ml of the standard was transferred to a 2 ml GC crimp cap vials and capped immediately. 0.20 ml of the sample was transferred to a 2 ml GC crimp cap vial with low volume insert (0.25 ml) and capped immediately. The experimental conditions of the GC instrument were as follows:

Carrier gas flow, Helium: 2.0 ml/min
Oven temperature program: 40° C. for 6 minutes then 20° C./min to 240° C. for 4 minutes
Injector temperature: 225° C.
Split ratio: 10:1
Detector: FID
Detector temperature: 250° C.
Hydrogen flow rate: 30 ml/min
Air flow rate: 400 ml/min
Make up gas flow rate (He): 25 ml/min The experimental conditions of the automatic liquid injector were as follows:

Solvent pre washes: 3
Sample pumps: 3
Solvent post washes: 3
Injection volume: 1 ml The column was conditioned at 250° C. for at least one hour prior to use.

One injection of each standard and two replicate injections of the sample solution were performed in addition to blank injections in the following order:

1. Blank
2. Calibration standard
3. Calibration standard
4. Blank
5. Sample, replicate 1
6. Sample, replicate 2
7. Blank The concentration of each analyte, $C_{sample}$, was calculated in µg/ml using the following formula:

$$C_{sample} = \frac{A_{sample} \times C_{std}}{A_{std}}$$

where:
$A_{sample}$: Peak area of the analyte in sample
$C_{std}$: Concentration of the analyte in calibration standard (µg/ml)
$A_{std}$: Peak area of the analyte in calibration standard, average of 2 injections (1ix) Aluminium Concentration Aluminium concentration was determined by inductively coupled plasma atomic emission spectroscopy (ICP-AES).

(1x) Radiochemical Parameters

Radiochemical purity (RCP) and radioactive concentration (RAC) of $^{18}$F-FACBC were measured.

RCP was determined by thin layer chromatography (TLC). The TLC strip was eluted using a mobile phase consisting of acetonitrile:methanol:water:acetic acid, 20:5:5:1 v/v. The RCP and any radiochemical impurities including $^{18}$F-fluoride were reported as percentages of the net sum of all peaks.

(1xi) Results

The following results were obtained:

| Production # | RAC (MBq/ml) | RCP(%)T0 | MeCN (µg/ml) | Al (µg/ml) |
|---|---|---|---|---|
| 1 | 1915 | >99 | 506 | 14 |
| 2 | 1804 | >99 | 324 | 14 |
| 3 | 1950 | >99 | 302 | 13 |
| 4 | 1698 | >99 | 89 | 15 |
| 5 | 1570 | >99 | 596 | 17 |
| 6 | 1815 | >99 | 218 | 15 |

Example 2: Synthesis of $^{18}$F-FACBC Using Inventive Method

2(i) Modified Sequence

A modified FASTlab™ cassette was used, as illustrated in FIG. 1. The sequence described in Example 1 was used except that the sequence included the extra heating/purging of the reaction vessel. The hydrolysis step was replaced with two steps, the first step of which included hydrolysis and in parallel heating of the reactor at 85° C., nitrogen purging (600 mbar HF) of the reaction vessel and vacuum (−600 mbar). The second step also included hydrolysis but heating of the reaction vessel was stopped. Nitrogen purging (600 mbar HF) and vacuum (−600 mbar) were used for cooling of the reaction vessel. Furthermore, the alumina SPE was removed and the sequence was changed to transfer the product directly to the formulation buffer vial after the HLB cartridge step.

2(ii) Analysis

The analysis methods as described in Example 1 were used.

| Production # | RAC (MBq/ml) | RCP(%)T0 | MeCN (µg/ml) | Al (µg/ml) |
|---|---|---|---|---|
| 7 | 3112 | 99.1 | 20 | 0.7 |
| 8 | 3900 | 99.1 | 20 | 0.8 |
| 9 | 1631 | 99.1 | 21 | 1.3 |
| 10 | 731 | 99.9 | 22 | 0.8 |
| 11 | 1831 | 99.8 | 25 | 0.8 |
| 12 | 1654 | 99.9 | 24 | 1.3 |
| 13 | 1573 | 99.1 | 21 | 1.1 |
| 14 | 1750 | 99.4 | 23 | 1.1 |
| 15 | 788 | 99.0 | 19 | 1.1 |
| 16 | 1023 | 99.2 | 17 | 1.1 |

The invention claimed is:

1. A method of preparation of a PET tracer composition in a cassette system having an end of synthesis (EOS) radiochemical purity (RCP) of at least 95%, comprising
   (a) reacting in a reaction vessel of the cassette system a source of $^{18}$F-fluoride with a precursor compound of Formula I:

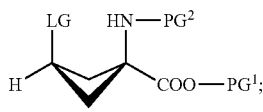

(I)

wherein:
LG is a leaving group;
PG$^1$ is a carboxy protecting group;
and, PG$^2$ is an amine protecting group;
wherein said reacting step is carried out in acetonitrile;
to obtain a reaction mixture comprising a compound of Formula II:

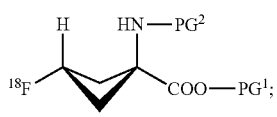

(II)

wherein PG$^1$ and PG$^2$ are as defined for Formula I;
   (b) transferring said reaction mixture comprising said compound of Formula II out of said reaction vessel onto a reversed phase solid phase cartridge of the cassette system and carrying out removal of PG$^1$ to obtain a reaction mixture comprising a compound of Formula III:

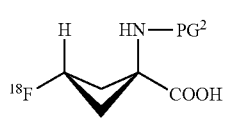

(III)

wherein PG$^1$ is as defined for Formula I;
   (c) applying heat to said reaction vessel to remove residual solvent from the reaction vessel at the same time as carrying out removal of PG$^1$ on the reversed phase solid phase cartridge;
   (d) transferring said reaction mixture comprising said compound of Formula III from the reversed phase solid phase cartridge back into said reaction vessel and carrying out removal of PG$^2$ to obtain a reaction mixture comprising $^{18}$F-FACBC;
   (e) purifying said reaction mixture comprising $^{18}$F-FACBC by passing it through a hydrophilic lipophilic balanced (HLB) solid phase, wherein said purifying does not comprise passing the reaction mixture comprising $^{18}$F-FACBC through an alumina solid phase, wherein the purified reaction mixture is obtained in steps (c) or (e) with citrate buffer, wherein said composition comprises no more than 5.0 µg/mL dissolved aluminium (Al) and no more than 25 µg/mL acetonitrile (MeCN).

2. The method as defined in claim 1 wherein LG is a linear or branched C$_{1-10}$ haloalkyl sulfonic acid substituent, a linear or branched C$_{1-10}$ alkyl sulfonic acid substituent, a fluorosulfonic acid substituent, or an aromatic sulfonic acid substituent.

3. The method as defined in claim 2 wherein LG is methanesulfonic acid, toluenesulfonic acid, nitrobenzenesulfonic acid, benzenesulfonic acid, trifluoromethanesulfonic acid, fluorosulfonic acid, or perfluoroalkylsulfonic acid.

4. The method as defined in claim 1 wherein LG is trifluoromethanesulfonic acid.

5. The method as defined in claim 1 wherein PG$^1$ is a linear or branched C$_{1-10}$ alkyl chain or an aryl substituent.

6. The method as defined in claim 5 wherein PG$^1$ is methyl, ethyl, t-butyl or phenyl.

7. The method as defined in claim 6 wherein PG$^1$ is methyl or ethyl.

8. The method as defined in claim 7 wherein PG$^1$ is ethyl.

9. The method as defined in claim 1 wherein PG$^2$ is a carbamate substituent, an amide substituent, an imide substituent or an amine substituent.

10. The method as defined in claim 9 wherein PG$^2$ is t-butoxycarbonyl, allyloxycarbonyl, phthalimide, or N-benzylideneamine.

11. The method as defined in claim 10 wherein PG$^2$ is t-butoxycarbonyl.

12. The method as defined claim 1 which is automated.

13. The method as defined in claim 1 wherein step (c) of applying heat to said reaction vessel is carried out at a temperature of 80° C.-140° C.

14. The method as defined in claim 1 wherein step (c) of applying heat to said reaction vessel is carried out at a temperature of 85° C.-130° C.

15. The method as defined in claim 1, said composition comprises no more than 20 µg/mL acetonitrile (MeCN).

16. The method as defined in claim 1, wherein step (c) comprises cooling the heated reaction vessel using nitrogen purging followed by application of vacuum.

* * * * *